United States Patent [19]

Burghart et al.

[11] Patent Number: 4,836,223

[45] Date of Patent: Jun. 6, 1989

[54] CIGARETTE SMOKING DEVICE

[75] Inventors: Heiner Burghart, Holm; Hans Behncke, Hamburg, both of Fed. Rep. of Germany

[73] Assignee: Heinrich Burghart Elektro- und Feinmechanik GmbH, Fed. Rep. of Germany

[21] Appl. No.: 927,587

[22] Filed: Oct. 17, 1986

[30] Foreign Application Priority Data

Oct. 19, 1985 [DE] Fed. Rep. of Germany ....... 3537287

[51] Int. Cl.⁴ .............................................. A24C 5/60
[52] U.S. Cl. ...................................... 131/329; 73/38; 73/865.1
[58] Field of Search ................... 131/329; 73/38, 865.1

[56] References Cited

PUBLICATIONS

DIN-specification 10 240 and translation of relevant portions, British Search Report—Nov. 20, 1986.

*Primary Examiner*—V. Millen
*Attorney, Agent, or Firm*—Lowe, Price, Leblanc, Becker & Shur

[57] ABSTRACT

A smoking-down device for cigarettes, wherein a piston in a smoking-down cylinder is driven by an electric stepping motor which receives a series of FM pulses per operating cycle of the smoking-down cylinder from a digital control system based on a micro-computer. Their mean frequency determines the suction or "puff" period, their total number of pulses determining the suction volume and their modulation graph determining the suction or puff pattern of the operating cycle. All three parameters may be preset with great precision and without interaction using digital signals, via the control system.

14 Claims, 3 Drawing Sheets

CIGARETTE SMOKING DEVICE

BACKGROUND OF THE INVENTION

1. Field of the Invention

The invention relates to a cigarette smoking device of the type comprising a smoking cylinder with an inlet and outlet valve, means including a smoke separator for connecting a cigarette to be smoked to an inlet side of the cylinder, a piston in the smoking cylinder, an electric motor and a post-connected transmission for imparting reciprocating movement to the piston and an electrical control system for generating a variable feed voltage for the electric motor.

2. Description of the Prior Art

The smoking-down of cigarettes for analytical and mensuration purposes in described in particular in DIN specificaton No. 10240. Devices of the kind referred to in the foregoing, so-called automatic smoking machines, are utilised for the smoking-down operation. The piston in the smoking cylinder of the smoking machine performs a working cycle for each puff taken at the cigarette which is to be smoked down. The draw or puff period, i.e. the duration of the suction stage of the working cycle, and the draw or puff volume, i.e. the dimension of the suction stroke, should be adjustable. Furthermore, a particular puff pattern or cycle should be followed during each puff.

In a known device of the kind referred to in the foregoing, the piston of the smoking clinder is actuated by a uniformly operating d.c. motor via a crank gear. This establishes a sinusoidal puff or suction pattern. The variation of the suction period is performed by analogous variation of the rotational speed of the d.c. motor. A variation of the suction volume is possible only by a mechanical shift of the eccentric of the crank gear. The momentary setting has to be verified by means of test runs during which the suction volume is rechecked. The suction pattern is invariably fixed.

In another known smoking device, the piston is moved in the smoking cylinder by means of a uniformly operating d.c. motor via a rack and pinion gear. This establishes a rectangular suction pattern. The adjustment of the suction period occurs as before by means of speed change of the d.c. motor, the adjustment of the suction volume occurring by means of a mechanical variation of the terminal position of the piston. In this case too, the adjustment of the suction volume has to be verified on test runs and the suction pattern is invariably fixed as a structural parameter.

In the case of the known devices, it is consequently impossible to operate with different suction patterns or cycles in one device. Any change in the suction period affects the suction volume and vice-versa, so that setting up modified values becomes very protracted.

SUMMARY OF THE INVENTION

It is an object of a cigarette smoking device in which different suction patterns as well as different suction periods and suction volumes may easily be set at will.

According to the invention, this object is achieved in that the electric motor is constructed as a linear stepping motor and in that—as a supply voltage per operating cycle of the smoking cylinder—the control system generates a frequency-modulated series of pulses for its suction stage, the total number of pulses, the mean frequency and the modulation pattern being adjustable to allow adjustment of the suction volume, of the suction period and of the suction pattern.

In the device of the invention, the suction pattern, suction period and suction volume are preset in purely electrical manner, that is to say by means of a digital signal, whose individual pulses are converted direct into corresponding motion by the stepping motor. A complex transmission, such as has been required until now to generate a particular suction pattern may thereby be omitted from the mechanical section of the device. Different suction patterns, selected in a purely electrical manner in the simplest way, may be applied at will in the same device. The same applies regarding the setting of suction period and suction volume. The three variables, being the suction pattern, the suction period and the suction volume, are represented in a very uncomplicated way by three different parameters of a single signal, namely by the modulation pattern, the mean frequency and the total number of pulses of a frequency-modulated pulse series, and may concomitantly be altered independently of one another. The device according to the invention thereby for the first time broaches possibilities of mensuration and analysis based on very complex smoking actions and down to smoking of a single cigarette by puffs of different volume, different suction period based on different smoking patterns.

The suction stage of each working cycle of the smoking device is determined by the frequency-modulated pulse sequence. In a preferred embodiment the return of the piston to its terminal position at the end of the blowout or exhaust stage is also performed by means of a digital signal. In this connection, it is accomplished by the terminal position sensor or pickup, that the control over the return displacement may be exercised independently of the corresponding duration of the stroke of the preceding suction displacement.

The control system advantageously comprises a control computer based on microprocessor technology, the different modulation or suction patterns being stored in program form and being called up under application of software. It is thus possible to react rapidly to users' requests regarding particular suction patterns by a comparatively uncomplicated program alteration. At the same time, all the other functions of the smoking device, such as the switching-over of the inlet and outlet valve or the scanning of the terminal position sensor may also be controlled via the computer.

A further preferred embodiment of the invention is based on the principle that a pulse train is intially generated for each working cycle or puff, which always comprises a specified number of pulses preferably counted under application of software, notwithstanding all other settings. The suction period is initially established by adjusting the frequency of this pulse train on the suction period divider. The total number of pulses is of such magnitude that the stepping motor performs the suction phase with the mechanically optimum stroke upon receiving all the pulses. A particular and adjustable percentage proportion of the pulses is removed from the pulse train in another step, by means of the suction volume divider. This does not alter the period of duration of the pulse train, but reduces the number of steps performed by the stepping motor and correspondingly, the piston stroke and thereby the suction volume. The final pulse sequence is finally generated in a third step from the pulse train by frequency modulation as a function of the required suction pattern or cycle, by again dividing the pulse train by means of the suction cycle divider, now however under adjustment repeated throughout the suction stage of the divisional ratios according to the suction cycle, the mean value of the divisional ratios of suction cycle being identical for all suction cycles. The latter is again preferably performed under application of software, whilst suction cycle dividers have successively fed to them a series of stored separating dividers which for their part represent a particular preselected suction pattern or cycle. The suction volume divider and the suction cycle divider may also be interchanged to the same effect in the functional sequence.

According to a further embodiment the whole device can be controlled from the outside by digital means, e.g. by means of a superordinated computer, that is to say regarding the setting of the suction period, volume and pattern variable for each puff, as well as of the operating sequence.

A uniformly transmitting gear is preferred as a transmission because this prevents non-linear variations by the gear of the electrically preset suction parameters. Furthermore, the mechanical structure is uncomplicated.

Further objects and advantages of the invention will become apparent from the following detailed description taken in conjunction with the accompanying drawings which illustrate a preferred embodiment of the invention.

DETAILED DESCRIPTION OF THE PREFERRED EMBODIMENT

Figure 1:
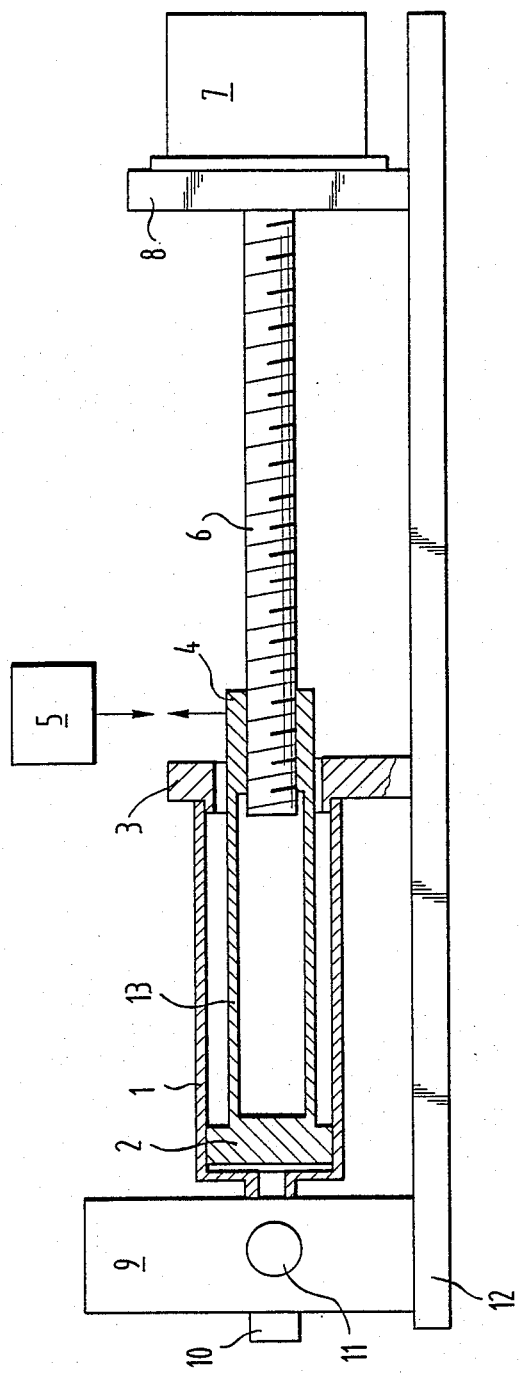
FIG. 1 shows the electromechanical section of a cigarette smoking device in a diagrammatical sideview.

According to FIG. 1, a cigarette smoking device incorporates a smoking cylinder 1 with a piston 2 situated therein. The smoking cylinder 1 is firmly installed in horizontal alignment on a mounting plate 12 by means of a bracket 3. The piston 2 is integrally provided with a tube 13 concentric with respect to the smoking cylinder 1, which at extremity of the smoking cylinder 1 adjacent the bracket projects out of the cylinder and merges into a spindle nut 4. The spindle nut 4 has an inner thread and co-operates with a long spindle 6 which house an outer thread and is the output spindle of an electric stepping motor 7. The latter is equally firmly installed on the mounting plate 12 by means of a bracket 8. The piston 2 is moved reciprocatingly in the smoking cylinder 1 by rotation of the spindle 6 in the one direction or the other.

FIG. 1 shows the piston 2 in its idle or terminal position, in which it is situated at the beginning of a working cycle of the device. This terminal position is detected by a terminal position sensor 5 which co-operates with the spindle nut 4 of the piston 2 and reacts in the terminal position referred to with the piston 2 against the end of the smoking cylinder 1.

The smoking cylinder 1 is connected via an aperture in its axial end to an electrically energisable inlet and outlet valve 9 which is also installed on the mounting plate 12. The inlet and outlet valve 9 has an inlet connector 10 to which the cigarette which is to be smoked down is connected in a manner not shown in particular, via a smoke trap or separator, as well as an outflow connector 11 through which occurs the discharge of the gaseous phase during the smoking operation.

Figure 2:
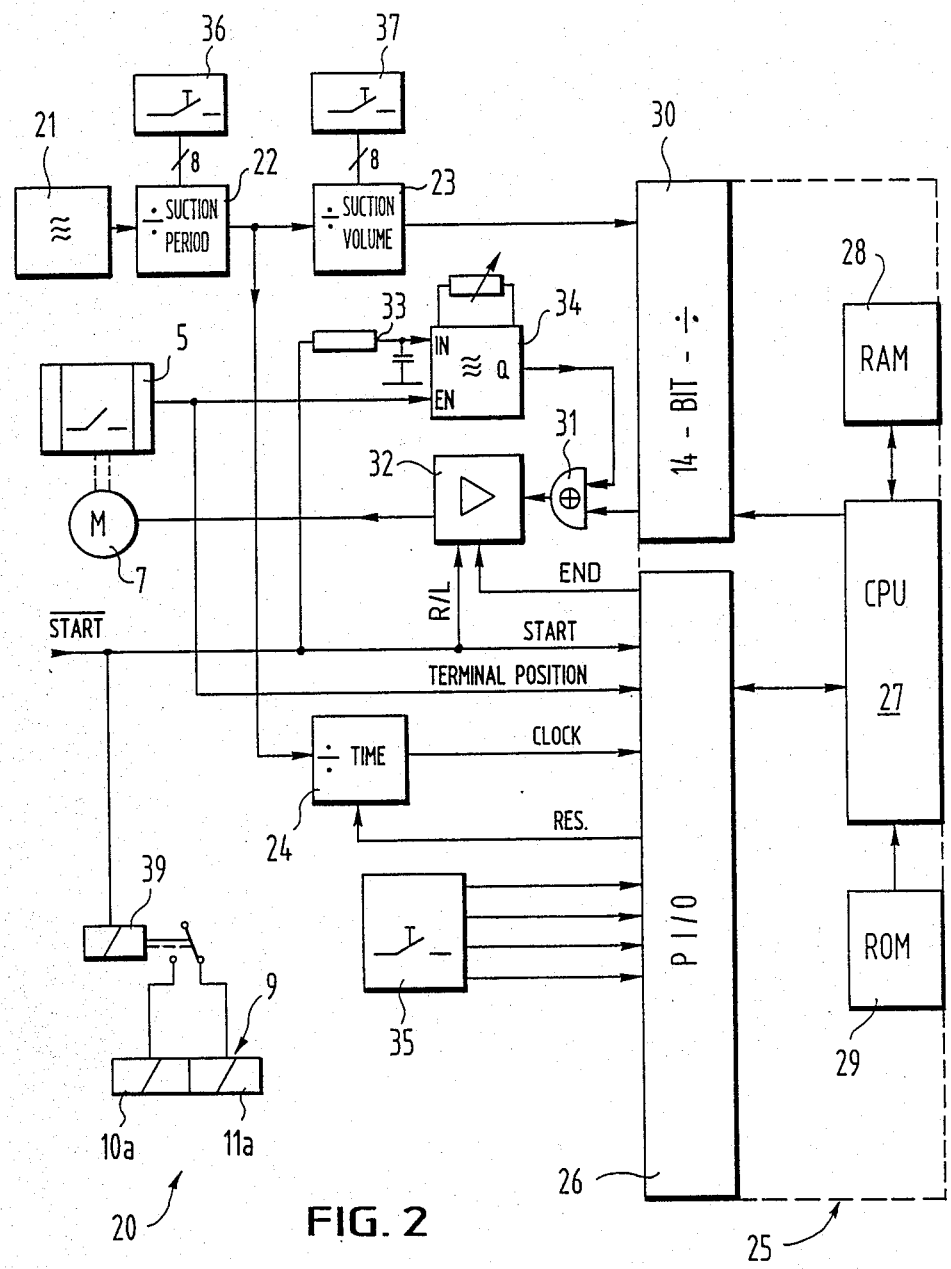
FIG. 2 shows a block circuit diagram of the electrical control system of the smoking device of FIG. 1.

The electric stepping motor 7 is energised, in a manner to be explained in detail below, by means of an electrical control system 20 according to FIG. 2, so that the piston 2 is displaced reciprocatingly in the smoking cylinder 1. Whilst doing so, each working cycle of the piston represents a puff on the cigarette which is to be smoked. During the suction stage, i,e. during displacement of the piston 2 from its terminal position in the direction towards the right in FIG. 1, the inlet side of the inlet and outlet valve is opened by appropriate electrical energisation, so that the cigarette is acted upon by the negative pressure generated by the piston 2. During the return displacement of the piston 2 into the terminal position, i,e. during the exhaust stage, the outlet side of the valve 9 is open towards the exhaust stub 11. The electrical control system 20 shown in FIG. 2 comprises a quartz oscillator 21, which may for example deliver clock pulses at a fixed frequency of 19.6608 mc/s. The pulses reach a suction period divided 22 of which the divisor may be adjusted by means of a tow-digit "BCD" signal. The "BCD" signal arrives either from a manually controllable setting member 36 or from a superordinated control computer. The divisor is set according to the required suction period or rather the duration of the suction stage. For example, a divisor of 20 corresponds to a suction period of 2.0 seconds. The output of the suction period divider carries a pulse train whose frequency is inversely proportional to the suction period set.

This pulse train reaches another divider, being a suction volume dividier 23, in which the dividing factor is adjustable by means of a two-digit "BCD" signal. This "BCD" signal may also be obtained either from a manually controllable setting member 37 or from a superordinated control computer. As a function of its adjustment, the suction volume divider 23 suppresses a part of the pulse of the pulse train supplied, so that the pulse train at its output has a numner of pulses reduced in accordance with the fraction set, for example to 40% of the pulses supplied.

The pulse train coming from the pulse period divider 22 moreover reaches a time divider 24 having a fixed dividing factor of for example $2^{15} = 1/32768$. The output pulses of the time divider 24 travel as timing or clock pulses to the input-output component 26 of a single board computer 25 which also comprises an 8-bit microprocessor 27 (CPU), a random access memory 28 for storage of transient data and a read-only-memory 29. The read-only-memory 29 contains an operating program as well as a series of numeric values with which particular modulation or suction patterns are illustrated in a manner to be explained. The computer 25 also has a processor controlled 14-bit divider 30

The 14-bit divider 30 is acted upon on its input side by the pulse train coming from the suction volume divider 23. Its output pulses travel via an OR circuit 31 to a driving circuit 32 for the stepping motor 7. The driving circuit 32 furthermore receives a start signal fed in from the outside, which also travels to the input-output component 26 and via a timing element 33 to a voltage-controlled oscillator 34. The output of the oscillator 34 is connected to a second input of the OR member 31. The terminal position signal coming from the terminal position sensor 5 is recieved at a control input terminal by the oscillator 34.

The selection of a particular suction pattern is performed by means of a manually controlled setting member 35 which feeds a digital selection signal corresponding to the selection via four data channels to the input-output component 26. Alternatively, the election signal may originate from a superordinated control computer.

A relay 39 activated by the start signal alternately switches an inlet-side magnetic coil 10a and a outlet-side magnetic coil 11a of the inlet and outlet valve 9 in such a way that the inlet 10 is open for the duration of the atart signal, and that the outlet 11 is open otherwise.

A working cycle of the piston 2, or rather a "puff", is triggered by the onset of the start signal. With its onset, the computer begins to count the clock pulses coming from the time divider 24. At the same time, it frees the output of the 14-bit divider 30 so that the stepping motor 7 receives stepping pulses via the driving circuit 32 from this instant onwards in accordance with the pulse sequence generated at the output of the 14-bit divider, and commensurately moves the piston 2 during the suction stage. The computer 25 counts the clock pulses coming from the time divider 24 and terminates the output of the 14-bit divider 30 which an a specific number of clock pulses determined once and for all, e.g. 60, is reached. This means that the suction volume divider 23 always receives the same number of input pulses for all suction operations, being 1,966,080 pulses notwithstanding the momentary setting of the suction period divider 22. Of these, the 14-bit divider again reaches a proportion corresponding to the setting of the suction volume divider, e.g. 786,432 pulses at a setting of 40%. The total number of pulses of 1,966,080 in the example is of such magnitude that the stepping motor displaces the piston 2 through the maximum mechanically possible stroke, which yields the maximum possible suction volume. The stroke and thus the section volume may be reduced by adjusting the suction volume divider. The setting of the suction period divider 22 acts solely on the frequency of the clock pulses and thus on the suction period. The suction volume remains unchanged. Conversely, the setting of the sucton volume divider has no bearing on the frequency of the clock pulses and thus on the suction period.

The number of pulses is again scaled down on the 14-bit divider 30. A particular suction pattern selected via the suction pattern selector 35 is generated by the fact that the divisional factor of the 14-bit divider 30 is reset at each clock pulse, the divisional factors successively coming into application, being stored in the read-only memory 29 as already stated. 60 divisional factors are stored for each suction pattern in the numerical example specified. The divional factors stored are so determined numerically that the man value of all divisional ratios of a suction pattern is the same for all suction patterns, in other words that the pulse sequence obtained at the output of the 14-bit divider 30 is always the same irrespective of the suction pattern selected in each case, and depends only the suction volume set. The mean value of the divisional ratios amounts to be 100/23977 in the numerical example, so that the total number of pulses amounts to 8200 at maximum volume. The almost constant adjustment of the divisional ratio of the 14-bit divider 30 results in a corresponding frequency-modulation of the pulse sequence and thus in a displacement of the piston 2 during the suction stage, corresponding to the required section pattern.

Upon termination of the start signal, the driving circuit 32 is switched over to the opposite direction of motor rotation, and the voltage-controlled oscillator 34 is switched on. The pulses thereupon reaching the drive circuit 32 via the OR gate 31 cause the return displacement of the piston 2 until it has reached its terminal position again, at which the terminal position sensor 5 deactivates the oscillator 34. An operating cycle is them completed.

Figure 3:
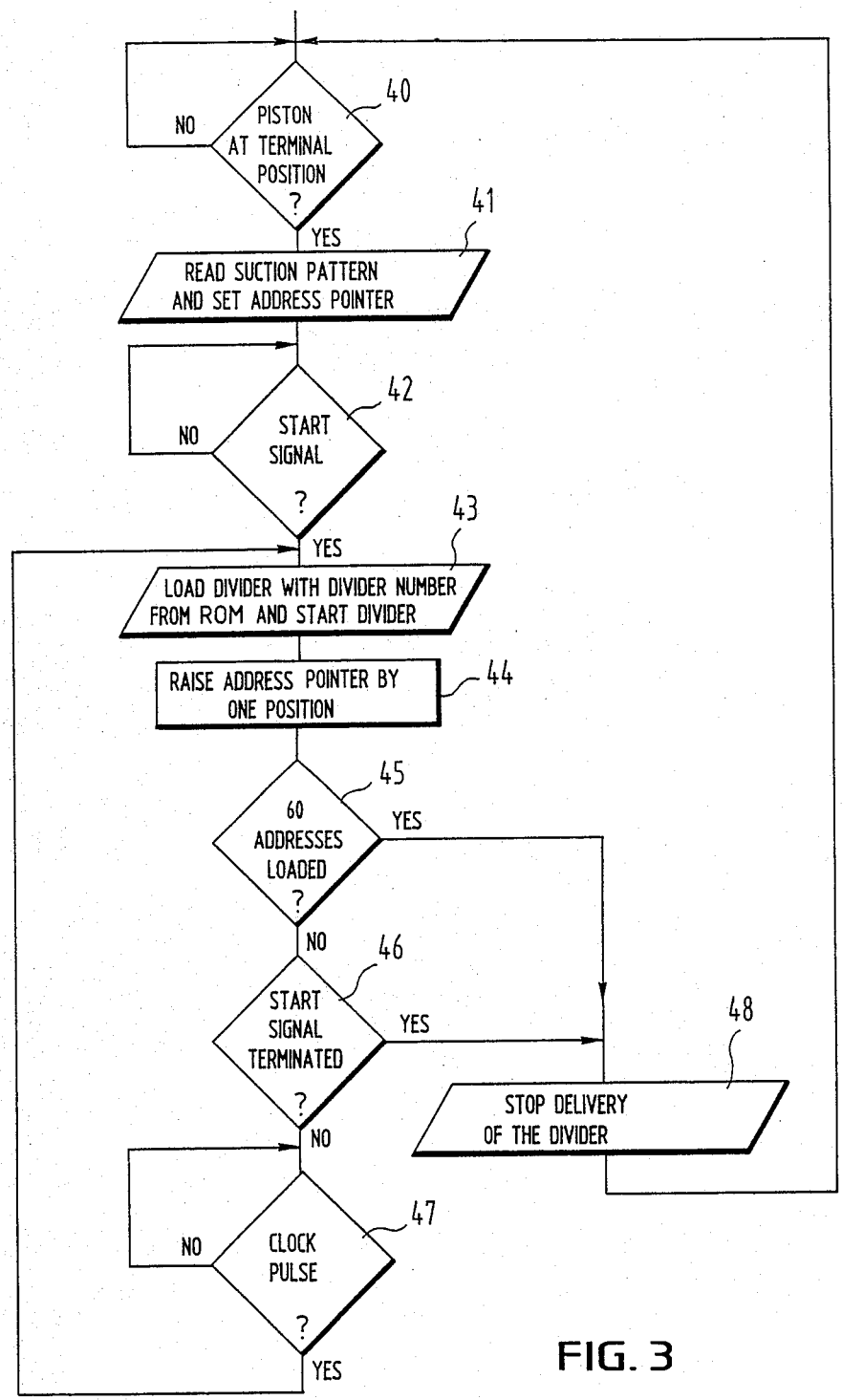
FIG. 3 shows flow diagram limited to the essential functions, for the control system according to FIG. 2.

The stages of an operating cycle under application of software are described briefly with reference to FIG. 3. During the stage 40, the computer 25 checks whether the piston 2 is present in its terminal position. If this is not the case, the check is repeated. If it is the case, the working step 41 is performed, during which the suction pattern selector 35 is scanned and an address pointer is set up. During the following stage 42, a check is run on whether a start signal had been applied. If this is not the case, the check is repeated. If it is the case, the divisor determined by the address pointer, that is to say the initial first divisor of the suction pattern selected is transferred during the operating step 43 from the read-only-memory 29 into the 14-bit divider 30, and the latter is placed in operation. The address pointer is raised by one position thereupon, during another step 44. A check is then made during stage 45 on whether 60 addresses had already been loaded. If this is not the case, a check is made during stage 46 on whether the start signal had been terminated. If this is not the case either, a check is made during stage 47 on whether another clock pulse is present. If this is not the case, the check is repeated. If it is the case, the operating steps and stages 43 to 47 are passed through, in another loop. If the check during stage 45 demonstrates that all 60 addresses had been loaded, or during stage 46 that the start signal had been terminated, the pulse delivery of the 14-bit divider 30 is stopped during the operating step 48, and the initial state at the beginning of stage 40 is then reverted to.

What is claimed is:

1. A cigarette smoking device comprising a smoking cylinder with an inlet and an outlet valve, means including a smoke separator for connecting a cigarette to be smoked to an inlet side of the cylinder, a piston in the smoking cylinder, a linear stepping electric motor and a post-connected transmission for imparting reciprocating movement to the piston and an electrical control system for generating a variable feed voltage for the electric motor, wherein the control system generates a frequency-modulated series of pulses for its suction stage, the total number of pulses, the mean frequency and the modulation pattern being adjustable to allow adjustment of the suction volume, of the suction period and of the suction pattern.

2. The device of claim 1, wherein said piston is provided with a terminal position sensor for the terminal position of a blow-out stage, and wherein said control system generates a pulse voltage for the stepping motor following each FM pulse series until the terminal position sensor reacts.

3. The device of claim 1, wherein said control system comprises a programmed microprocessor having memories and an input and output component, and wherein the modulation patterns available for selection are stored in program form.

4. The device of claim 1, wherein said control system incorporates a fixed-frequency oscillator and a post-connected suction period divider with a separating divider adjustable according to the required suction period, and wherein the pulse series is formed from the output pulses of the suction period divider and in each case last until a constant specified number of output pulses of the suction period divider is obtained.

5. The device of claim 4, wherein said suction period divider has post-connected to it a suction volume divider having a division factor adjustable according to the required fraction of the maximum suction volume, the pulse series being formed from its output pulses.

6. The device of claim 5, wherein said suction volume divider has post-connected to it a suction cycle divider whereof the output pulses form the pulse series and whereof the divisional ratio is periodically repeated during each pulse series and re-adjusted according to a program-selected specific suction pattern.

7. The device of claim 5, wherein said suction period divider and said suction volume divider are in each case organised for adjustment by an external digital control signal fed direct to the divider.

8. The device of claim 7, wherein said external signal originates from a manually operable setting element.

9. The device of claim 7, wherein said external signal originates from a superordinated control computer.

10. The device of claim 3, wherein the suction pattern applied in each case may be selected by means of a digital selector signal fed to the input-output component.

11. The device of claim 10, wherein said digital selector signal originates from a superordinated control computer.

12. The device of claim 10, wherein said digital selector signal originates from a manually operable setting element.

13. The device of claim 1, wherein said transmission comprises a uniformly transmitting gear.

14. The device of claim 13, wherein said transmission comprises a spindle transmission.

* * * * *